United States Patent [19]
Paoli et al.

[11] Patent Number: 5,872,361
[45] Date of Patent: Feb. 16, 1999

[54] TURBIDIMETER WITH NON-IMAGING OPTICAL CONCENTRATOR

[75] Inventors: Ernie R. Paoli, Loveland, Colo.;
Stephen K. Wilcken, Seattle, Wash.;
Richard P. Kolman, Loveland, Colo.

[73] Assignee: Hach Company, Loveland, Colo.

[21] Appl. No.: 823,089

[22] Filed: Mar. 24, 1997

[51] Int. Cl.$^6$ .................................................... G01N 21/49
[52] U.S. Cl. .................... 250/341.8; 250/574; 356/334
[58] Field of Search ............................. 250/341.8, 343,
250/574; 356/339, 338, 340, 442

[56] References Cited

U.S. PATENT DOCUMENTS

| | | | |
|---|---|---|---|
| 5,237,386 | 8/1993 | Harley | 356/339 |
| 5,506,679 | 4/1996 | Cooper et al. | 356/339 |
| 5,589,935 | 12/1996 | Biard | 356/339 |

FOREIGN PATENT DOCUMENTS

| | | | |
|---|---|---|---|
| 0141039 | 8/1984 | Japan | 356/339 |

OTHER PUBLICATIONS

Hinterberger & Winston, "Use of a Solid Light Funnel to Increase Phototube Aperture . . ." Rev. of Scientific Inst. vol. 39 No. 8 p. 1717, Aug. 1968.

*Primary Examiner*—Edward P. Westin
*Assistant Examiner*—Richard Hanig
*Attorney, Agent, or Firm*—Dean P. Edmundson

[57] ABSTRACT

A turbidimeter is described for measuring the turbidity of a liquid. The turbidimeter includes (a) a sample cell for the liquid to be tested, (b) an optical source such as a light-emitting diode (LED) for producing a light beam directed at the sample cell; (c) an optical detector, and (d) non-imaging optical concentrator located between the sample cell and the optical detector for concentrating light scattered by the liquid in the sample cell. The optical concentrator is preferably integral with the sample cell holder and it exhibits a sharp field of view which minimizes the effect of stray light in the instrument. The optical detector means produces a signal in response to the amount of scattered light it detects. The signal is converted to a turbidity value which is displayed. The turbidimeter can be battery powered and is small and compact.

21 Claims, 8 Drawing Sheets

TURBIDIMETER WITH NON-IMAGING OPTICAL CONCENTRATOR

FIELD OF THE INVENTION

This invention relates to devices and techniques for measuring turbidity of liquids. More particularly, the invention relates to turbidimeters. Even more particularly, this invention relates to a portable turbidimeter which employs an optical means for gathering and concentrating light scattered by turbid media.

BACKGROUND OF THE INVENTION

Turbidimeters are devices used to detect and measure light scattered by turbid media when a beam of light is directed through the media. A conventional turbidimeter includes a light source, a sample cell, and an optical detector at a predetermined position and orientation (usually 90°) with respect to the light source and the sample being tested. The optical detector produces a relatively low-level analog signal in response to the presence of turbid media, with the signal being proportional to the turbidity of the sample. The signal generated by the detector is amplified by low-bandwidth electronics to levels consistent with output electronics, chart recorders, etc.

A typical use for turbidimeters is in measuring the clarity of drinking water. In the United States, USEPA Method 180.1 regulates turbidimetric instruments and procedures used for quality control of drinking water. In Europe, ISO 7027 regulates turbidimetric instruments and procedures. Laboratory and on-line process control turbidimeters of the type regulated by USEPA Method 180.1 and ISO 7027 are marketed by several companies, notably by Hach Company.

USEPA Method 180.1 and ISO 7027 regulate various aspects of the optical design of turbidimeters, including the wavelength of the illuminating beam. Method 180.1 mandates an incandescent lamp with a color temperature of between 2200° K. and 3000° K., a peak detected wavelength between 400 and 600 nm, and an unspecified optical bandwidth. On the other hand, ISO 7027 specifies a peak wavelength of 860 nm and a bandwidth of 60 nm, but does not specify the particular type of light source which may be used. This has resulted in the recent introduction of ISO 7027-compliant turbidimeters which comprise solid-state light sources, such as IRLEDs (infrared light-emitting diodes).

IRLEDs are much more robust and reliable than incandescent lamps. In addition, IRLEDs are small and consume little electrical power. Such advantages are commensurate with the design of hand-held battery-operated turbidimetric instruments. Unfortunately, the available optical power in a collimated beam from a typical IRLED will generally be lower than is available in a collimated beam from an incandescent lamp. Therefore, the signal processing circuitry in an IRLED-based instrument intended for use in making low-level turbidimetric measurements (e.g., for drinking water) per ISO 7027 will require higher levels of signal amplification, as compared with the signal processing circuitry in a Method 180.1 turbidimeter. The increased level of signal amplification required in an IRLED-based instrument may result in increased susceptibility to stray light and EMI, with possible adverse effects on the dynamic range.

In prior art turbidimeters, susceptibility to stray light is reduced by placing apertures in the illuminating beam at locations which serve to confine the illuminating beam to a geometrically well-defined area. The detector is then placed outside the path of the main beam. The detector may be placed behind additional apertures to help eliminate secondary stray light. Usually, however, some stray light will find its way to the detector by means of multiple scattering paths.

The desired effect of the apertures is to eliminate sources of stray light which appear within the field of view of the detector. Ideally, the field of view of the detector should be quite large, in order to efficiently collect the turbidimetric signal which originates in a "cloud of light" generated by the presence of the illuminating beam within the sample. At the same time, the effective optical collection area of the detector should also be large. The product of the effective optical collection area of the detector times the solid angle representing the field of view is a measurement of the optical efficiency or throughput, sometimes called the etendue.

It is desirable to maximize the etendue in order to reduce the required level of signal amplification, but only if the majority of stray light remains outside the field of view of the detector. In a properly-designed turbidimeter, most stray light originates at or beyond the locations where the illuminating beam enters and exits the sample cell or compartment. Therefore, as viewed from the location of the detector, there is (or should be) a relatively well-defined angular separation between the field of view comprising the turbidimetric signal and regions outside this field which contain the stray light component. Thus, it is desirable to implement means for achieving a sharp cutoff in the field of view of the detector. It is apparent that the unapertured detectors commonly used in prior art turbidimeters do not have the required sharp field of view cutoff characteristics. The use of one or more apertures in front of the detector, also common practice in the prior art, compromises etendue and reduces the sensitivity of the instrument.

It is evident that stray light-limiting apertures work relatively well in conditions where there are large spaces and long optical paths, such as in prior art process control or laboratory turbidimeters. However, in a hand-held instrument, the distance from the collimating lens to the location of the sample, and from the sample cell to the detector, is quite limited, with insufficient room for effective use of apertures.

Thus, the optical design of prior art turbidimeters does not adequately address the need for simultaneous large field of view, large effective optical collection area, and sharp angular (field of view) cutoff. These features are especially important for compact hand-held IRLED-based instruments, where the optical power in the illuminating beam is somewhat less than has been available with the use of incandescent lamps, and where there is insufficient room for effective use of apertures to reduce the level of stray light.

SUMMARY OF THE INVENTION

It is therefore an object of this invention to utilize, within a turbidimeter, a class of optical device known as a non-imaging concentrator, to increase the etendue of the photodetector while at the same time achieving a sharp angular (field of view) cutoff. It is a further object of this invention to utilize a non-imaging concentrator as the optical means to increase the amount of turbidimetric scattered light signal received by the photodetector in a turbidimeter, thereby improving the signal-to-noise ratio in IRLED-based turbidimeters. It is a further object of this invention to utilize the sharp field of view cutoff characteristics of non-imaging concentrators to aid in the elimination of stray light which arrives at high angles of incidence. Unlike apertures, which are impractical for use in a compact hand-held turbidimetric instrument, the particular optical properties and effectiveness of non-imaging concentrators are size invariant. It is therefore a further object of this invention to utilize the scalability of non-imaging concentrators in a small optical package, consistent with the dimensions which are characteristic of a hand-held turbidimetric instrument.

In accordance with a preferred embodiment of the present invention there is provided a portable turbidimeter which is sufficiently small and compact that it can be carried in the user's pocket when desired and which is very easy to use and is accurate for measuring turbidimetry of liquids such as water. The portable turbidimeter is battery powered and comprises:

(a) a sample cell;

(b) optical source means comprising a light-emitting diode (LED), a collimating lens, and preferably a monitor detector means;

(c) optical detector means; and (d) a non-imaging optical concentrator located between the sample cell and the optical detector for concentrating the scattered light from the sample cell and defining a sharp field-of-view for scattered light.

The turbidimeter also includes electronic circuitry and software, including: (1) an amplifier that conditions the output of the optical detector, (2) an analog-to-digital converter that converts the amplifier output to digital format, (3) a microprocessor and software that converts the output of the analog-to-digital converter to turbidity units, (4) a display to indicate the turbidity level to the user, (5) an LED controller means which compares an adjustable portion of the monitor detector output to a reference, thus standardizing the optical detector output at a reference turbidity value, and (6) operator controls to allow for turbidimeter calibration as well as reading of the sample turbidity. Preferably the LED optical source emits radiation having a wavelength of 860 nm. It is also preferable for the sample cell to include flat or planar opposing side walls such that the field of view of the optical concentrator is limited to the flat side walls of the cell, whereby the edges of the cell which generate stray light are out of the field of view of the optical concentrator.

The turbidimeter of the invention is very sensitive and very accurate. The small and compact size of the instrument enables it to be carried in the user's pocket to any desired location for testing liquids.

Other features and advantages of the invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
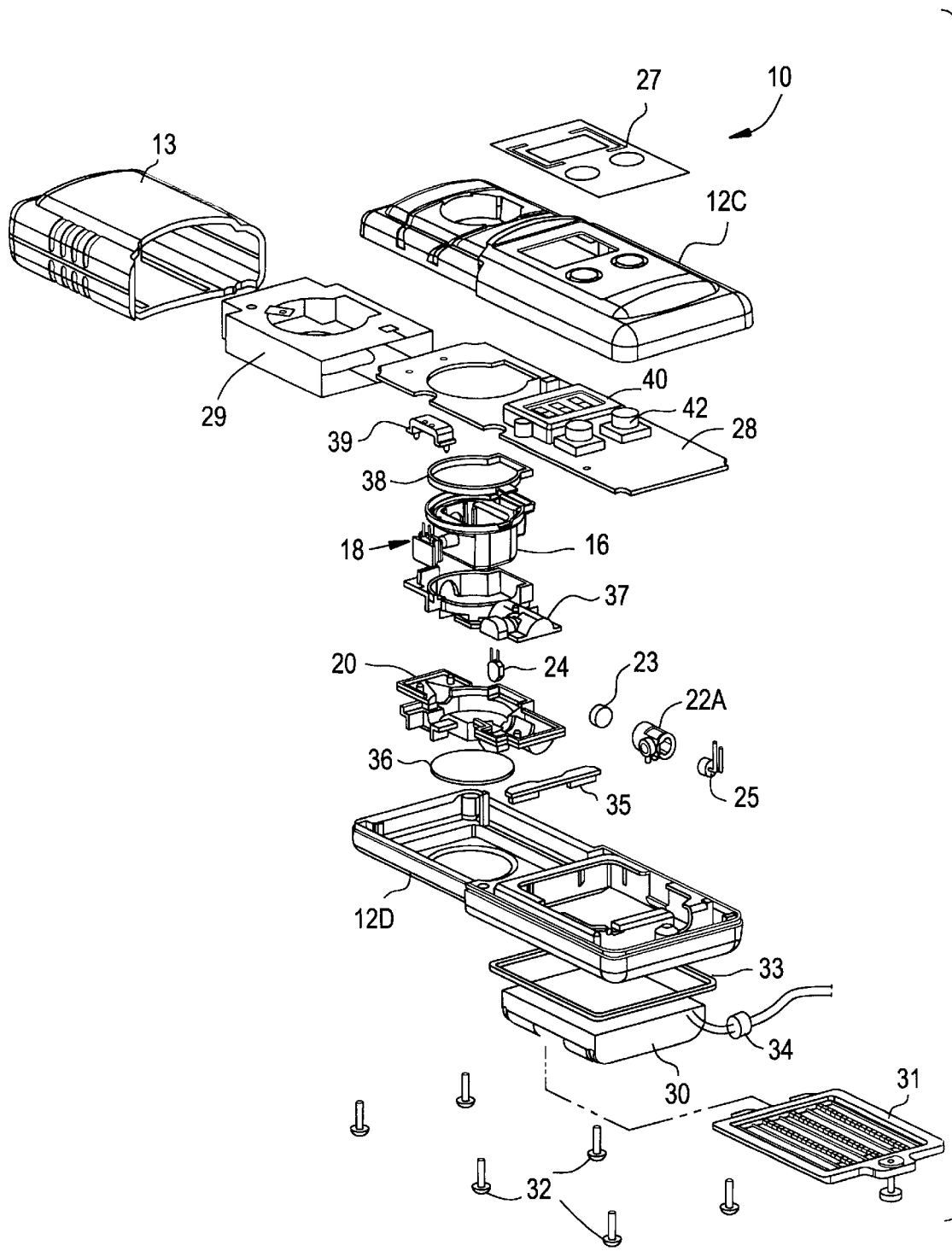
FIG. 1 is an exploded view of a portable turbidimeter of the invention.

In the drawings there is shown a preferred embodiment of turbidimeter 10 of the invention. This turbidimeter is small, compact and very portable. It may even be carried in the user's pocket, if desired.

Figure 2:
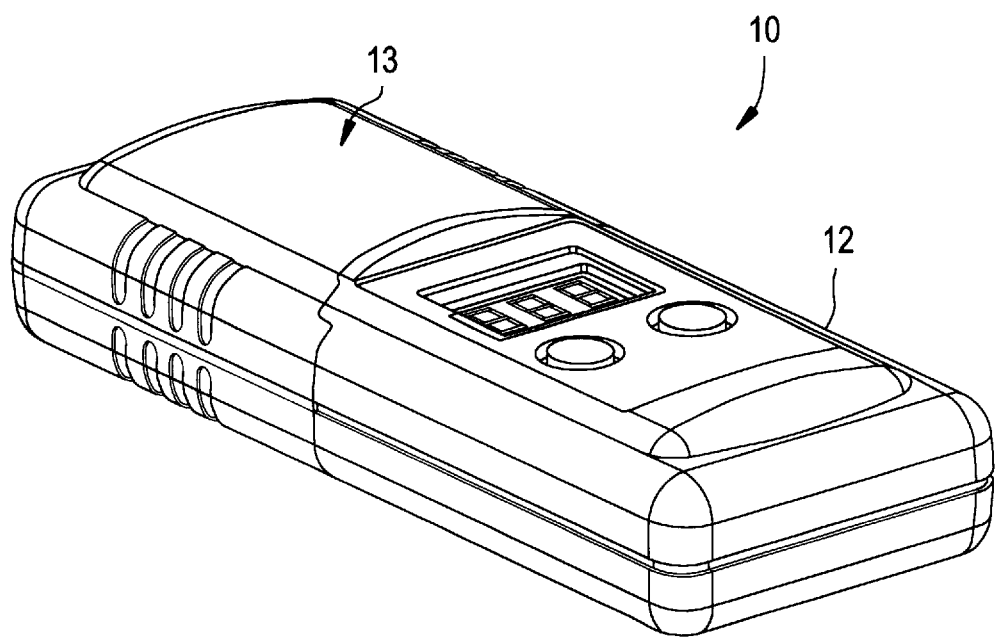
FIG. 2 is a perspective view of the assembled instrument of FIG. 1.
Figure 3:
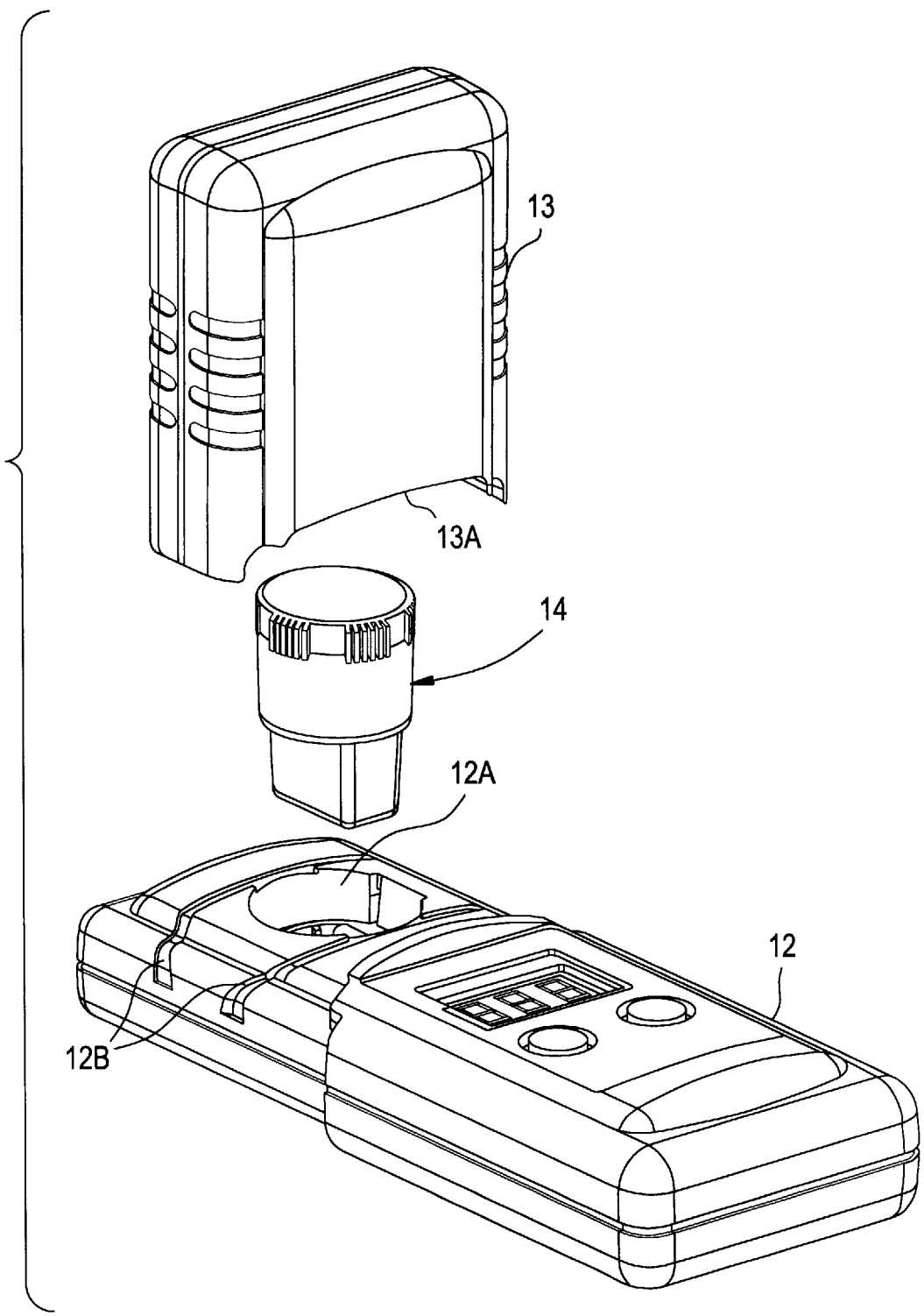
FIG. 3 is a perspective view of the instrument illustrating the loading of a sample cell into the cell receiving port.
Figure 4:
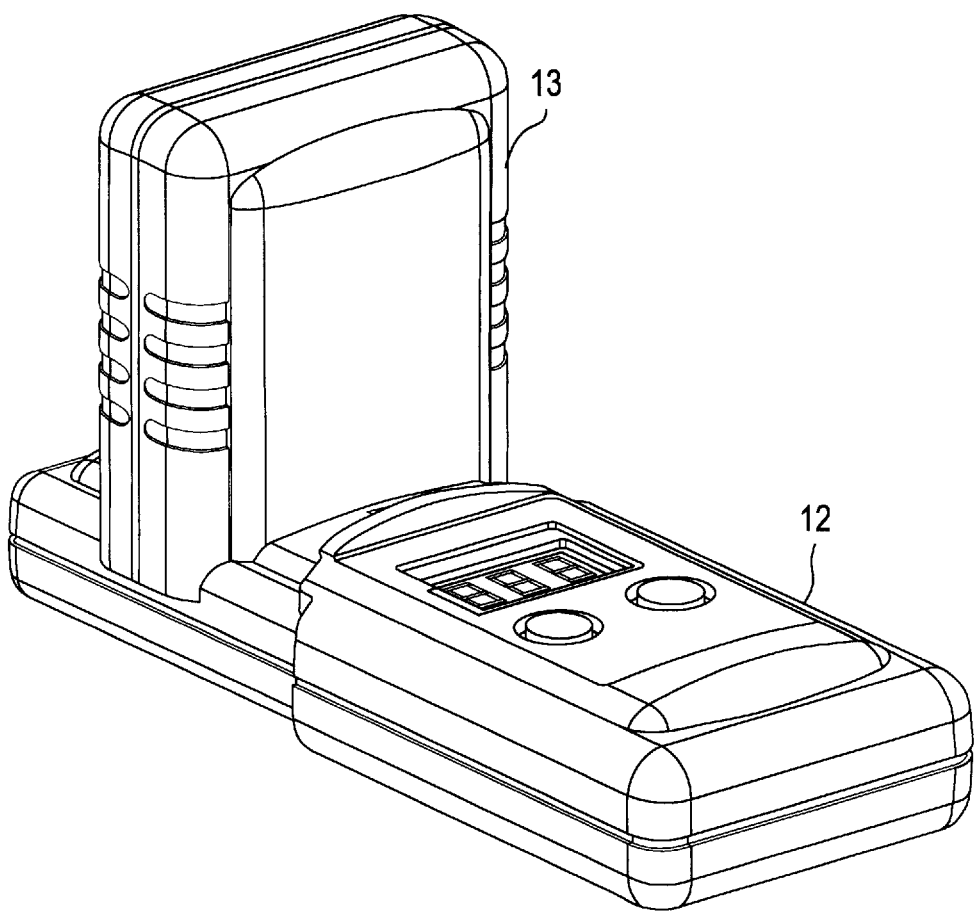
FIG. 4 is a perspective view of the instrument with the cover over the sample cell for testing.

The turbidimeter comprises a case or enclosure 12 and a removable sleeve or cover member 13. When the cover slidably engages one end of the instrument (as shown in FIG. 2), the sample cell receiving port is protected and the instrument can be easily carried on the person. When the cover 13 is removed, the sample cell receiving port 12A in the instrument is exposed and available for inserting a sample cell 14 therein, as illustrated in FIG. 3. After the sample cell has been slidably received in port 12A, the cover 13 can be oriented in the manner shown in FIG. 3 and placed over the receiving port and the sample cell so as to block ambient light and prevent it from entering the receiving port. Enclosure 12 preferably includes transverse grooves or recesses 12B for receiving the lower edges 13A of cover 13. FIG. 4 shows the cover 13 in a resting position on enclosure 12 enabling testing of a sample in the sample cell. As illustrated, the longitudinal axis of the cover 13 is perpendicular to the longitudinal axis of the enclosure 12 when the sample cell is in the receiving port.

Figure 5:
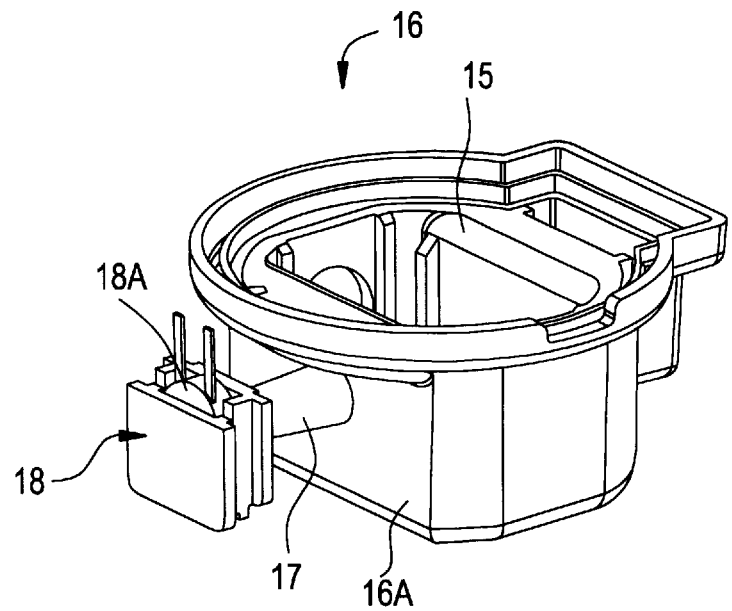
FIG. 5 is a perspective view of the sample cell cup with optical concentrator and optical detector.

FIG. 5 is a perspective view of a preferred embodiment of sample cell holder or cup 16, shroud 15, optical concentrator means 17, and optical detector means 18. Preferably the cup 16 includes a planar side wall or face 16A to which the optical concentrator means 17 is integrally secured. The optical detector means 18 preferably comprises a light detector 18A whose face is bonded or adhered directly to the outer end of the concentrator means 17. This is also illustrated in the side view of FIGS. 9 and 10.

Non-imaging concentrator means 17 is comprised of the "theta-in theta-out" variety of compound parabolic concentrator (CPC) known in the art. See, for example, *High Collection Nonimaging Optics*, Welford and Winston, San Diego Academic Press, 1989, incorporated herein by reference. This form is only one of many possible non-imaging concentrator geometrical forms comprising various sections of cones, parabolas, hyperbolas, etc. The optical properties of various non-imaging concentrator geometrical forms may be more or less suitable for a particular turbidimeter embodiment. An appropriate concentrator geometry will be one which yields high etendue, high optical concentration, and a sharp cut-off in field-of-view, within the overall size constraints of the instrument.

FIG. 1 is an exploded view of the turbidimeter instrument 10 comprising upper and lower housing sections 12C and 12D which are secured together by fasteners 32. A battery holder 30 is included in the housing and is covered by door 31. Gasket 33 surrounds the battery holder. Ferrite bead 34 reduces interference from radiation from outside sources. A light block 36 is located below the base of the cup 16. A moisture seal 35 is located between the sample cell port and the battery holder. The optics module housing 22A holds the LED 25 and lens 23.

The upper and lower optics housings 37 and 20, respectively, enclose and accurately locate the optics module and monitor detector 24 and prevent ambient light from reaching the turbidimetric detector 18A. The sample cell holder or cup 16 is received and located in an appropriately-shaped opening in the optics housings. A gasket 38 rests on the upper edge of the cup 16. Cover 39 rests on top of the optical detector means 18. The optics housings also form the conical light trap which is designed to intercept and absorb the IR beam from the LED to greatly reduce stray light in the instrument.

Circuit board assembly 28 includes the necessary electronic circuitry for processing the signals from the optical detector to convert them to a turbidity display 40. Electrostatic discharge shield 29 surrounds the board assembly 28 and includes appropriate openings for receiving the sample cell cup. The instrument is controlled by key pad 42. Key pad overlay 27 rests on top of the housing section 12C.

Figure 6:
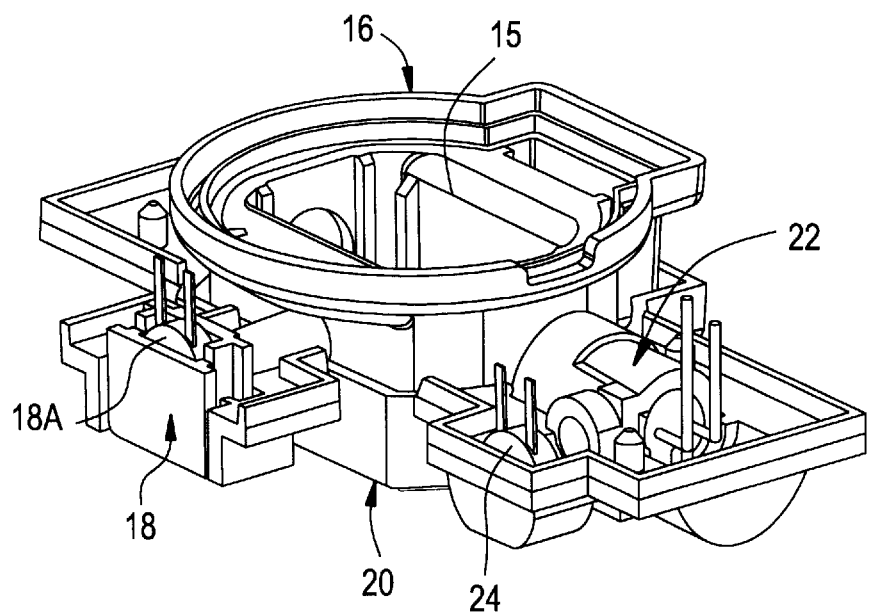
FIG. 6 is a perspective view of the bottom optical housing with the optics module, monitor detector sample cell cup, shroud, and 90° turbidimetric scattered light detector.

FIG. 6 shows a perspective view of the bottom housing 20 for the optics with the optics module 22 and monitor detector 24 located in place. The monitor detector 24 generates a photocurrent, based on energy produced by LED 25. A selectable portion of this photocurrent is compared by the LED drive circuitry to a fixed reference level, thus providing a stable, but adjustable, source of light energy. Therefore, the calibration of the turbidimeter is stabilized.

Figure 7:
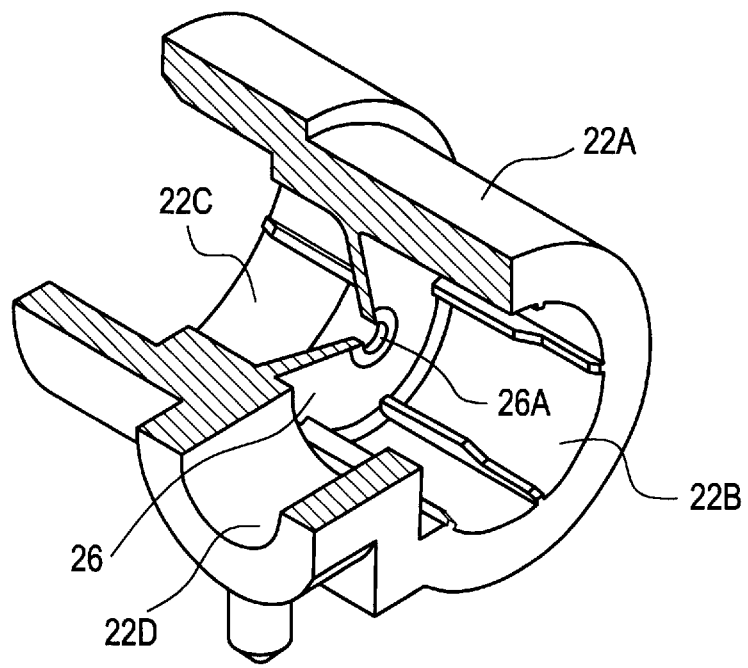
FIG. 7 is a perspective view, partially cut-away, of the optics module.

FIG. 7 shows the optics module enclosure 22A having open opposite ends 22B and 22C. End 22B is for receiving the LED 25 and end 22C is for receiving a collimating lens 23. Separating ends 22B and 22C is a wall 26 with a small central aperture 26A (e.g., 0.03 inch). Diverging light from LED 25 passes through aperture 26A, and is then collimated by collimating lens 23 which is secured in end 22C.

Optics module enclosure 22A serves the vital purpose of absorbing light emitted by LED 25, except that portion of light which passes through aperture 26A, and that portion of light which enters the monitor detector chamber 22D. In fulfillment of this purpose, optics module enclosure 22A is comprised of light absorbing material.

Collimating lens 23 is inserted into end 22C of optics module enclosure 22A such that the infinite conjugates side of the collimating lens is facing away from aperture 26A. The position of collimating lens 23 within end 22C is adjusted to project an 8× magnified image of aperture 26A at a distance of 1.5 inches. After 8× magnification, collimating lens 23 produces a 0.25 inch diameter focused image of a 0.030 inch diameter aperture. Aperture sizes smaller or larger than 0.030 inch will produce smaller or larger images, respectively. A larger aperture will illuminate a larger volume of sample. However, stray light may increase faster than the received turbidimetric signal. An appropriate figure of merit for aperture size must involve the achievable turbidimetric dynamic range. In other words, the best aperture size will yield the highest dynamic range of measurement. For the preferred embodiment, the best aperture size was determined experimentally to be 0.030 inch.

Figure 8:
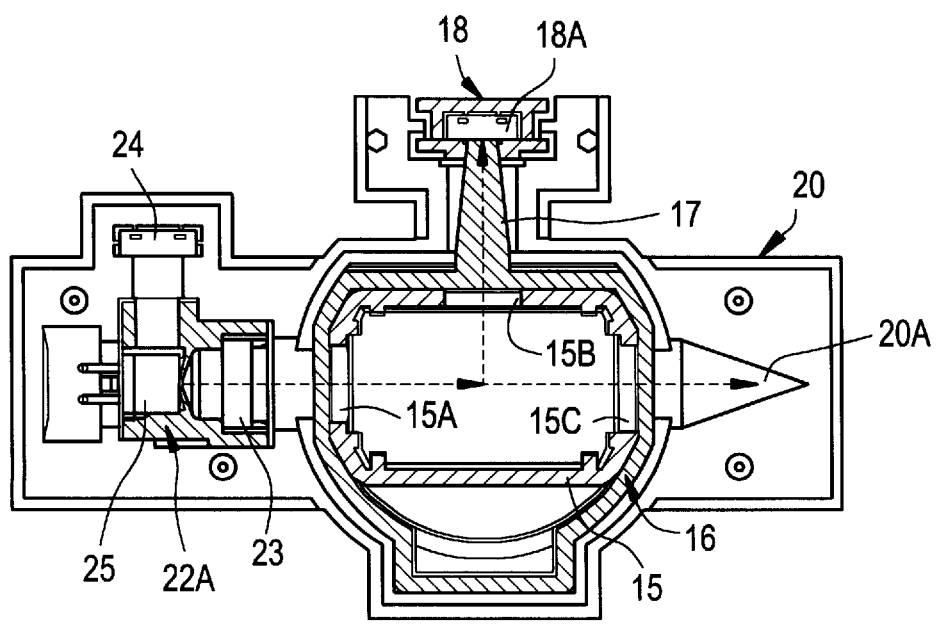
FIG. 8 is a top view, partially cutaway, showing the light source, sample cell holder, optical concentrator and optical detector in the bottom optics housing.

FIG. 8 is a top view, partially cut-away, showing the bottom optical housing with the optics module and sample cell holder and shroud. The LED 25 and lens 23 are shown in the optics module enclosure 22A. The monitor detector 24 and optical detector 18 are held in place in the bottom optics housing, as shown. The light path from the LED and the lens is shown by the arrows in FIG. 8. The light passes through the aperture 26A and is focussed onto the entrance of the conical light trap 20A in the bottom housing 20. Once the light leaves the lens, it passes through an aperture 15A in shroud 15 and enters the sample cell. Light scattered by particles in the liquid sample passes through a 90 degree aperture 15B in the shroud and enters the concentrator 17 where it is directed onto the active area of the optical detector means 18A. The light that is not scattered in the sample cell passes through an exit aperture 15C and into the light trap 20A. The inside of the light trap is polished to reduce stray light due to diffuse scattering from the surface of the cone.

Figure 9:
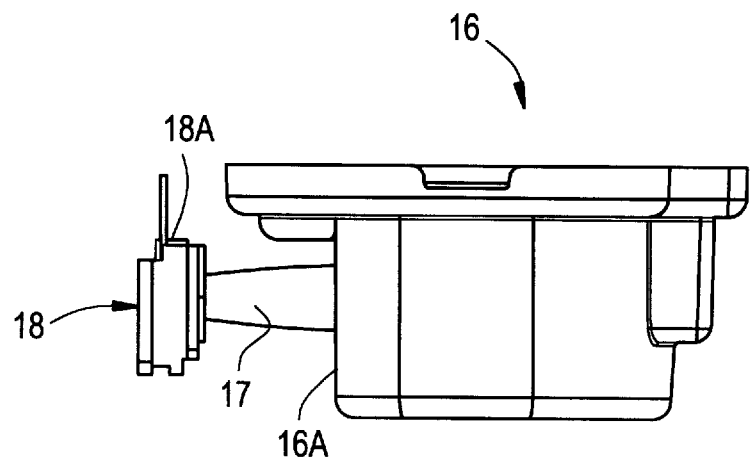
FIG. 9 is a side elevational view showing the sample cell holder, non-imaging concentrator, optical detector, and detector holder.
Figure 10:
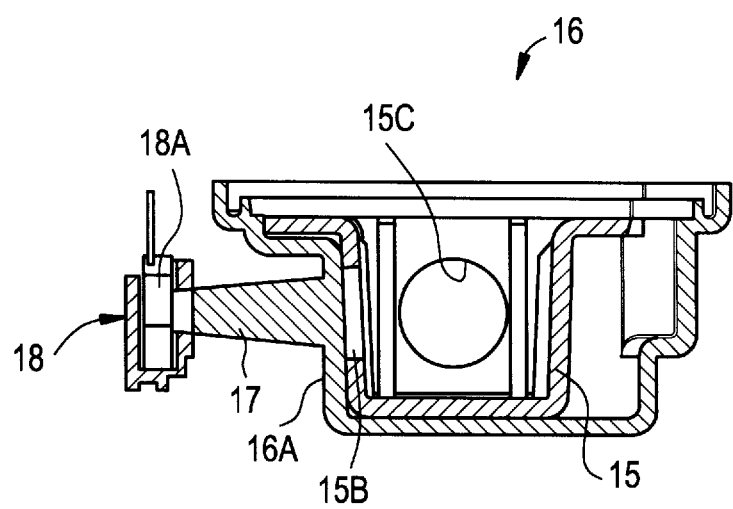
FIG. 10 is a cross-sectional view of the apparatus shown in FIG. 9.

FIGS. 9 and 10 show the sample cell holder, optical concentrator means, and optical detector means.

Figure 11:
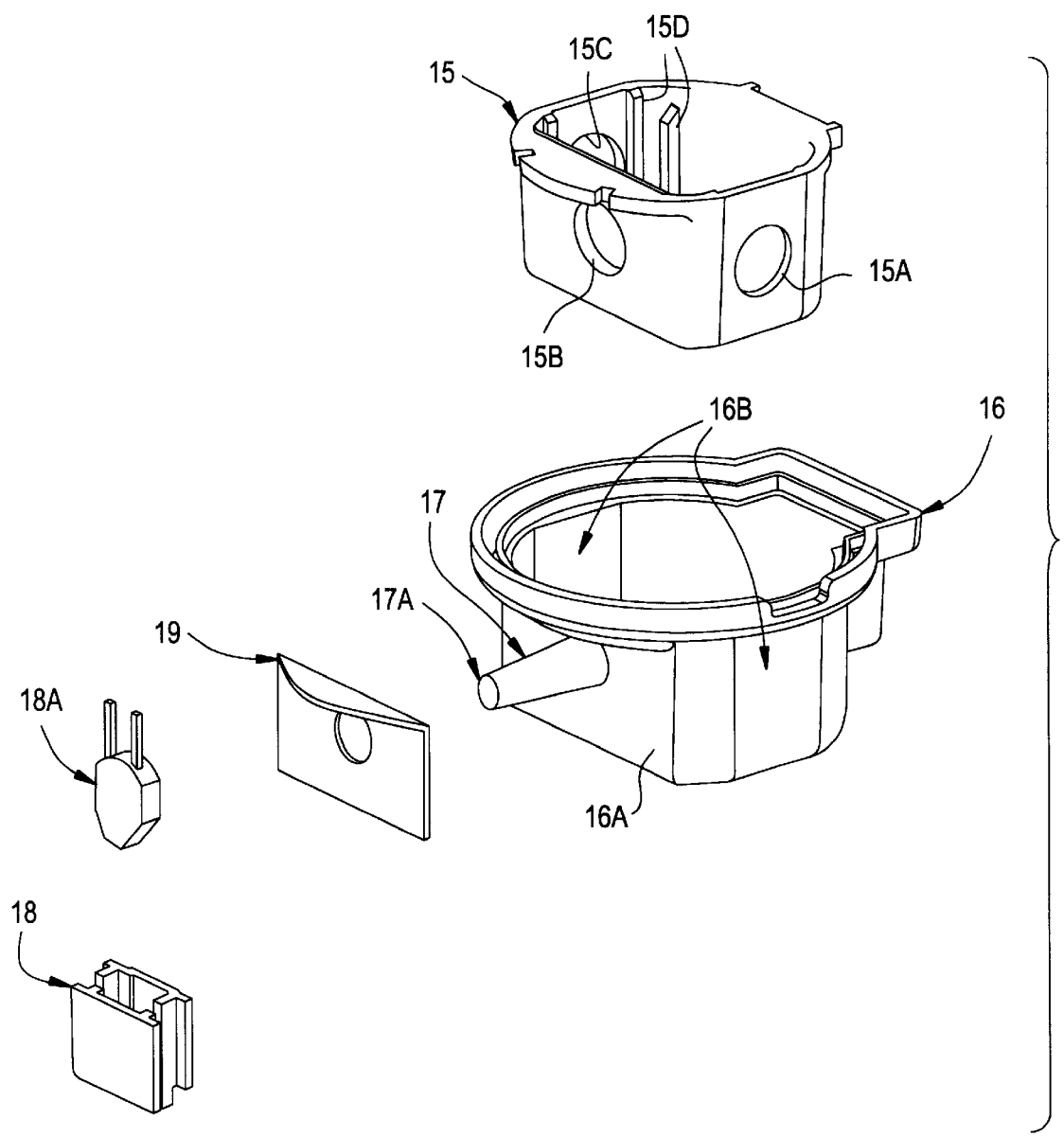
FIG. 11 is an exploded view of the preferred sample cell holder, shroud, optical concentrator and optical detector means.

FIG. 11 is an exploded view showing the various components of the sample cell holder 16, shroud 15 and optical detector means 18A and detector holder 18. A light blocking label 19 is intended to be secured to the planar face 16A of the holder or cup 16. The label 19 effectively eliminates stray light from entering the optical concentrator 17. The black plastic light shroud 15 is also bonded to the inside of the sample cell holder to further reduce the effects of "light-piping" by total internal reflection within the walls of cup 16. The detector 18A is pressed into the holder 18 and then the assembly is bonded onto the end 17A of the optical concentrator 17.

The shroud 15 locates the sample cell in the instrument by means of the tapered ribs 15D located on its inside corners. The shroud includes apertures for the entrance and exit of light energy, thus greatly minimizing stray light. The shroud also is responsible for elimination of parasitic stray light which is transferred through the cup assembly by means of total internal reflection. The walls of the shroud are opaque.

The opposing end walls 16B of the cup 16 are preferably parallel to each other and ar perpendicular to the light beam from the LED. These walls are transparent to the light beam.

Preferably the optical concentrator is composed of a high refractive index material such as "Lexan" polycarbonate type 141-111 (blue dyed to offset natural yellow tint).

The radius of the concentrator output aperture for the instrument shown herein is preferably 1.4 mm. A two-part epoxy optical adhesive is used to secure the concentrator to the face of the light detector means. If too little adhesive is used, optical coupling between the concentrator and the detector will be deficient. If too much adhesive is used, the light being conducted by the concentrator may travel around the adhesive fillet to areas outside the detector face.

Other variants are possible without departing from the scope of this invention.

What is claimed is:

1. A turbidimeter for measuring the turbidity of a liquid comprising:
   (a) sample cell for containing said liquid;
   (b) optical source means comprising a light-emitting diode for producing a light beam directed at said sample cell;
   (c) optical detector means; and
   (d) non-imaging optical concentrator means located between said sample cell and said optical detector means for concentrating light scattered by said liquid in said sample cell.

2. A turbidimeter in accordance with claim 1, further comprising battery means for powering said optical source means and said optical detector means.

3. A turbidimeter in accordance with claim 1, wherein said diode emits radiation having a wavelength of approximately 860 nm.

4. A turbidimeter in accordance with claim 1, wherein said sample cell is removable.

5. A turbidimeter in accordance with claim 4, wherein said sample cell includes two opposing planar side walls.

6. A turbidimeter in accordance with claim 4, further comprising a sample cell holder, and wherein said concentrator means is integral with said sample cell holder.

7. A turbidimeter in accordance with claim 6, wherein said cell holder includes a planar face, and wherein said concentrator means is integral with said planar face.

8. A turbidimeter in accordance with claim 1, wherein said optical source means further comprises a collimating lens for collimating light produced by said diode.

9. A turbidimeter in accordance with claim 8, wherein said detector means is integral with said concentrator means.

10. A turbidimeter in accordance with claim 1, wherein said optical concentrator means comprises a compound parabolic concentrator.

11. A turbidimeter in accordance with claim 6, further comprising a shroud member positioned in said sample cell holder, wherein said shroud member includes two opposing end walls and two opposing side walls; wherein said end walls include axially-aligned apertures therethrough; and wherein one of said side walls includes an aperture therethrough.

12. A turbidimeter in accordance with claim 8, further comprising an optics module in which said diode and said lens are secured; wherein said optics module includes an aperture for controlling passage of light from said diode to said lens.

13. A turbidimeter in accordance with claim 12, further comprising top and bottom optical housing sections enclosing said optics module; wherein said optical housing sections define a light trap.

14. A turbidimeter in accordance with claim 13, further comprising a sample cell holder; wherein said optical housing sections define an opening for receiving said sample cell holder; wherein said light trap is located adjacent to one side of said sample cell holder; and wherein said optics module is positioned adjacent to the opposite side of said sample cell holder.

15. A portable turbidimeter for measuring the turbidity of a liquid comprising:

(a) sample cell for containing said liquid;

(b) optical source means comprising a light-emitting diode for producing a light beam directed at said sample cell; and further comprising a collimating lens for collimating light produced by said diode;

(c) optical detector means positioned to detect light scattered at an angle of 90° to said light beam;

(d) non-imaging optical concentrator means located between said sample cell and said optical detector means for concentrating light scattered by said liquid in said sample cell;

(e) signal processing means for converting said signal from said optical detector means to a turbidity value; and (f) power means comprising a battery for powering said optical source means and said optical detector means.

16. A turbidimeter in accordance with claim 15, further comprising a sample cell holder, wherein said concentrator means is integral with said sample cell holder, and wherein said detector means is integral with said concentrator means.

17. A turbidimeter in accordance with claim 16, further comprising a shroud member positioned in said sample cell holder, wherein said shroud member includes two opposing end walls and two opposing side walls; wherein said end walls include axially-aligned apertures therethrough; and wherein one of said side walls includes an aperture therethrough.

18. A turbidimeter in accordance with claim 17, further comprising an optics module in which said diode and said lens are secured; wherein said optics module includes an aperture for controlling passage of light from said diode to said lens.

19. A method for measuring turbidity of a liquid in a sample cell comprising the steps of:

(a) providing optical source means comprising a light-emitting diode for producing a light beam and a collimating lens for collimating said light beam;

(b) directing said light beam at said sample cell;

(c) providing an optical detector means for producing a signal in response to scattered light detected; and (d) providing a non-imaging optical concentrator means and positioning it between said sample cell and said optical detector means for concentrating light scattered by said liquid in said sample cell.

20. A method in accordance with claim 19, wherein said optical detector means is positioned to detect light scattered at 90° relative to the path of said light beam.

21. A turbidimeter in accordance with claim 1, wherein said optical detector means produces a signal in response to detected light, and further comprising signal processing means for converting said signal from said optical detector means to a turbidity value.

\* \* \* \* \*